United States Patent
Rousseau et al.

(10) Patent No.: US 12,268,556 B2
(45) Date of Patent: Apr. 8, 2025

(54) MEDICAL IMAGING SYSTEM COMPRISING A FOLDABLE TOUCHSCREEN

(71) Applicant: SUPERSONIC IMAGINE, Aix-en-Provence (FR)

(72) Inventors: Etienne Rousseau, Aix en Provence (FR); Damien Majorel, Marseilles (FR)

(73) Assignee: SUPERSONIC IMAGINE, Aix-en-Provence (FR)

( * ) Notice: Subject to any disclaimer, the term of this patent is extended or adjusted under 35 U.S.C. 154(b) by 0 days.

(21) Appl. No.: 18/578,640

(22) PCT Filed: Aug. 19, 2022

(86) PCT No.: PCT/EP2022/073239
§ 371 (c)(1),
(2) Date: Jan. 11, 2024

(87) PCT Pub. No.: WO2023/025692
PCT Pub. Date: Mar. 2, 2023

(65) Prior Publication Data
US 2024/0315672 A1 Sep. 26, 2024

(30) Foreign Application Priority Data
Aug. 27, 2021 (FR) ...................... 2108988

(51) Int. Cl.
*A61B 8/00* (2006.01)
*G06F 3/01* (2006.01)
(Continued)

(52) U.S. Cl.
CPC .............. *A61B 8/462* (2013.01); *A61B 8/468* (2013.01); *A61B 8/54* (2013.01); *G06F 3/016* (2013.01);
(Continued)

(58) Field of Classification Search
CPC ........... A61B 8/462; A61B 8/468; A61B 8/54; G06F 3/016; G06F 3/0416; G06F 3/0486;
(Continued)

(56) References Cited

U.S. PATENT DOCUMENTS 10,318,042 B2   6/2019  Xu
2007/0232885 A1* 10/2007 Cook ................. G16H 30/40
                                           600/407

(Continued)

FOREIGN PATENT DOCUMENTS

EP      2842497 A1    3/2015
JP   2010-086064 A    4/2010

(Continued)

OTHER PUBLICATIONS

Nannini et al., "Polyclonal outbreak of bacteremia caused by Burkholderia cepacia complex and the presumptive role of ultrasound gel", The Brazilian Journal of Infectious Diseases 2015;19(5); 543-545.

(Continued)

*Primary Examiner* — Dmitriy Bolotin
(74) *Attorney, Agent, or Firm* — Merchant & Gould P.C.

(57) ABSTRACT

Examples of this disclosure include a medical imaging system having a control module, a foldable touchscreen with at least a first touchscreen section and a second touchscreen section extending from the first section and being tiltable relative to the first section. The control module has a watertight surface resistant to liquids and configured to be cleanable by disinfectant liquid on the first and second sections, and between the two sections. Other examples include a method for medical imaging that includes displaying a first image generated by the imaging system on the third section of the system, duplicating the first image, displaying the first duplicated image on at least one of the (Continued)

first section and the second section such that a user can at least one of mark an area on the latter and have annotation options, and in response, processing the first image using a predefined algorithm.

22 Claims, 5 Drawing Sheets

(51) Int. Cl.
    *G06F 3/041*     (2006.01)
    *G06F 3/0486*     (2013.01)
    *G06F 3/04883*     (2022.01)
    *G06F 3/14*     (2006.01)
    *G06V 10/25*     (2022.01)

(52) U.S. Cl.
    CPC .......... *G06F 3/0416* (2013.01); *G06F 3/0486* (2013.01); *G06F 3/04883* (2013.01); *G06F 3/1446* (2013.01); *G06V 10/25* (2022.01); *G06F 2203/04102* (2013.01); *G06V 2201/03* (2022.01)

(58) Field of Classification Search
    CPC ............... G06F 3/04883; G06F 3/1446; G06F 2203/04102; G06V 10/25; G06V 2201/03
    See application file for complete search history.

(56) References Cited

U.S. PATENT DOCUMENTS

| | | | | |
|---|---|---|---|---|
| 2011/0043434 | A1* | 2/2011 | Roncalez | G06T 7/0012 345/3.1 |
| 2015/0023030 | A1* | 1/2015 | Tsukamoto | G06F 1/1652 362/419 |
| 2015/0261259 | A1* | 9/2015 | Endo | H10K 59/12 361/679.06 |
| 2016/0007965 | A1* | 1/2016 | Murphy | A61B 8/06 345/173 |
| 2016/0054901 | A1 | 2/2016 | Yang | |
| 2016/0270764 | A1* | 9/2016 | Wodecki | A61B 8/4405 |
| 2018/0188775 | A1* | 7/2018 | Perelli | G06F 1/1679 |
| 2018/0188780 | A1* | 7/2018 | Perelli | G06F 1/1662 |
| 2018/0218859 | A1* | 8/2018 | Ligtenberg | G06F 3/0414 |
| 2019/0380683 | A1* | 12/2019 | Nordgren | A61B 8/54 |
| 2020/0264673 | A1* | 8/2020 | Kim | G06F 1/1652 |
| 2022/0137667 | A1* | 5/2022 | Kim | G06F 1/1686 361/679.21 |
| 2023/0046954 | A1* | 2/2023 | Jung | H04M 1/03 |
| 2023/0376075 | A1* | 11/2023 | Leite Gomes | G06F 1/1616 |

FOREIGN PATENT DOCUMENTS

| | | |
|---|---|---|
| JP | 2010-240072 A | 10/2010 |
| JP | 2011-512973 A | 4/2011 |
| JP | 2019-525794 A | 9/2019 |
| WO | 2009-109585 A1 | 9/2009 |
| WO | 2016007673 A2 | 1/2016 |
| WO | 2016148872 A1 | 9/2016 |
| WO | 2018-002272 A1 | 1/2018 |

OTHER PUBLICATIONS

French Search Report in Application FR2108988, mailed May 11, 2022, 6 pages.
PCT International Preliminary Report on Patentability and English translation for same in Application PCT/EP2022/073239, mailed Mar. 7, 2024, 13 pages.
International Search Report for PCT/EP2022/173239, with English translation, Nov. 25, 2022, 6 pages.
Notice of Refusal issued Dec. 27, 2024, in Japanese Patent Application No. 2024-512998 (with attached English-language Translation), 12 pages.

* cited by examiner

MEDICAL IMAGING SYSTEM COMPRISING A FOLDABLE TOUCHSCREEN

CROSS-REFERENCES TO RELATED APPLICATIONS

This application is a National Stage Application of PCT/EP2022/073239, filed on Aug. 19, 2022, which claims the benefit of priority to French Application No. FR2108988, filed Aug. 27, 2021, each of the above applications being incorporated herein by reference in its entirety. To the extent appropriate, a claim of priority is made to each of the above disclosed applications.

PRIOR ART

A medical imaging system usually comprises electronic means, for example a sensor and/or a probe for acquiring data from a patient, and a processor for processing the collected data. It may also include a control module for controlling the system, associated in particular with a user interface.

More particularly, the user interface may comprise information input means and/or output means. Examples of input means comprise tactile or mechanical input means (such as one or more buttons, dedicated screen areas, switches or rotary controls) and electronic input means, such as for example a touchscreen. Output means comprise for example optical output means (such as a screen, displays, LEDs, or more particularly a touchscreen), loudspeakers and tactile output means (such as a vibration device).

In particular, in the event that the medical system is used for imaging a medium being examined, for example a human or animal body, it is appropriate to offer for sale and supply the system with a screen and a plurality of touch input means or a touchscreen for controlling the system. Examples of such imaging systems comprise an optical imaging system, an ultrasound imaging system, a radiography system, a computed tomography system, a mammography system and the like.

DISCLOSURE OF THE INVENTION

The aim of the present disclosure is to provide a medical examination system and a method for medical examination using such a system which enables more reliable and faster disinfection, in particular of a control module of the system.

The present disclosure relates to a medical imaging system, the system comprising:
- a control module configured for controlling the system including an optionally foldable touchscreen with at least a first touchscreen section and a second touchscreen section extending from said first section and being tiltable relative to said first section, wherein
- the control module has a leaktight surface resistant to liquids configured to be cleanable by a disinfectant liquid on the first and second section, between the two sections, and on the sides.

By means of this system, a user can clean and/or disinfect any area that has been touched on the foldable touchscreen or which is near to this area with a disinfectant liquid (for example comprising alcohol, hydrogen peroxide, quaternary ammonium, sodium hypochlorite, or a combination thereof) in an effective and thorough manner. As a result, the time required for the disinfection can be reduced, which also indirectly reduces the time and cost of an examination procedure, since more examinations can be carried out using the same system, the time between two examinations being drastically reduced. In addition, the reliability of effective cleaning and disinfection and therefore the prevention of any contamination is increased.

In this context, it is possible in particular for the user to apply a sufficient amount of disinfectant liquid to the foldable touchscreen, as its surface prevents the liquid from penetrating the interior and therefore damaging the system internally.

In addition, the system can be controlled entirely via the foldable touchscreen, the user can avoid touching other areas of the system during operation, for example during an examination procedure.

Furthermore, since the two (or optionally three) sections can be connected without any borders between them, different visual effects and/or control functions become possible, which can make the system easier to use. As a result, an examination procedure can become more intuitive, more configurable and adaptable for the user and therefore faster.

The disinfectant liquid may comprise a spray and/or gel and/or vaporised mist. In addition, the liquid may contain various different viscosities.

The first and/or second section may be configured to function as a control and/or regulating element of the system.

As also described in the context of the figures, the first and the second section may have exchangeable functions. Therefore, each of the sections can be used according to the situation.

At least one of the touchscreen sections may be configured to display a user interface, the user interface optionally comprising:
- a setting option (for example complementary), and/or
- a control means, and/or
- all or part of the patient file and/or examination report. For example, this examination report may include an ongoing examination report, but also an old previous examination report or other patients with a similar profile.

The user interface may comprise an adaptive mode, in which the user interface is configured to position the control means according to one or more gestures of the user (for example previously predefined or configured by the user).

As a result, in adaptive mode, the user interface may not have any predefined positioning of the control means. In this mode, the control means can be positioned according to the gestures of the user. In other words, the position of the control means is not predefined or fixed, but can depend on the gestures of the user.

This allows the user interface to be positioned advantageously so as to adjust to the user, rather than the user having to adjust to the interface. In an advantageous manner, an operation that does not require the user to look directly at the interface, a so-called "blind" mode operation of the user interface, becomes possible, as described in more detail below.

For example, the gesture of the user can consist of placing a hand (for example the palm and/or one or more fingers or the whole hand) on the touchscreen or at least bringing the hand close to the touchscreen. In general, "placing the hand, palm or finger on the touchscreen" can signify "coming into direct or indirect contact with the touchscreen with the hand, palm or finger". The touchscreen may also be configured for example to operate when the user's hand is covered by a glove. Thus, indirect contact may be due to a glove.

Alternatively or additionally, the gesture of the user may consist of placing (and/or at least approaching) an external control device on the touchscreen. For example, the control device may be a mechanical button, and/or a control wheel (or a clickable roller) and/or a joystick.

As a result, the positioning of the control means may depend on the position in which the user has placed their hand and/or the external control device on the touchscreen. The control means may therefore always be positioned to as to adjust to the position of the user's hand.

Users can therefore place their hand anywhere on the touchscreen and operate the system without looking at the touchscreen, i.e. in a "blind" manner.

A specific control means (i.e. a specific command) can be attributed to a specific finger. In this way, the user can use this control means without needing to look at the touchscreen ("freeze" button associated with the thumb for example).

Optionally, by default or at the user's request, the touchscreen can display the functions of the various control means in order to provide additional feedback to the user. Sound feedback can also guide the user (click, for example).

The user interface can also comprise a predefined mode, in which the user interface is configured to position the control means in a predefined manner.

As a result, in the predefined mode, the position of the control means can be predefined, for example in the form of keyboard. This mode can be used temporarily or permanently, depending on the use made of the system and/or the user's preferences. It can also be activated in default mode, for example when the system is started up and no operating mode or examination procedure has yet been commenced. It should be noted that the control means in the predefined mode do not necessarily have to be same as in the adaptive mode. For example, in the adaptive mode, only a selection of control means can be used, as described below.

The touchscreen can be configured to simulate haptic effects, in particular a mechanical button (for example a click control), track ball, track pad, and/or in the form of a control means.

For example, the control means may comprise a button, a wheel and a track ball. The control means can be understood to be virtual or simulated means, as their structural and/or haptic properties (in addition to their visual appearance) are provided virtually by the touchscreen, but do not constitute distinct physical devices.

The control means can be defined by simulating a haptic and/or structural form of the control means on the touchscreen, for example a border indicating the start/end of a control means. For example, in the event that a control means is a haptic button, the simulated border hides the simulated button and may help a user to feel where the button is. Thus, blind use of the control module becomes easier and more reliable, which is very advantageous, particularly in examination rooms which are very often dark to facilitate the analysis of the images produced. To further assist the user, it is also possible to simulate a texture on the button which is different from the rest of the touchscreen. Thus, the user can recognize the button by touch without looking at it. In addition, haptic simulation can also make the user feel a movement of the button where it will be pressed, for example the sensation of pressing down. In the case of the trackball, it will simulate the sensation of turning on itself.

In the adaptive mode, the system and/or the control module may be configured to determine the position of a finger (or in particular the tip or the pad of the finger) according to the gesture made by the user and to position a control means at the determined position on the user interface.

Consequently, the user interface can be configured to position a control means in a position where it is determined that a finger (or in particular the pad of the finger) is touching (or approaching) the touchscreen.

Thus, the position can advantageously be determined as a function of the position where the hand is placed on or close to the touchscreen, in particular the palm and/or one or more fingers. For example, as a function of the surface touched by the palm, the size of the hand and therefore the position of the finger (or each of the fingers) can be estimated by the system or the control module. This is an automatic adaptation to the size, shape and position of the hand. A hand having only four fingers will thus benefit from an automatically adapted interface. It is also advantageously possible to detect whether it is the user's left or right hand and thus adjust the proposed interface. Furthermore, a type of finger (for example the index finger or thumb) touching the touchscreen can be identified according to the position of the palm and/or other fingers touching the touchscreen. This makes it possible to assign a specific control means or a specific command to a specific type of finger, for example a "freeze image" function to the thumb of this hand.

In adaptive mode, a selection or a group or a control means may be position as selected according to a selected operating mode (examination procedure) of the system.

As a result, the system and/or the control module can select only certain control means (i.e. certain commands) which are frequently used in the current operating mode. As these selected control means (for example up to five or even more in the case of combinations of gestures) can be positioned so as to correspond to the position of a single finger, the user can control the system blindly, simply by placing their hand anywhere on the touchscreen.

The foldable touchscreen may comprise a third touchscreen section extending from said second section and being tiltable relative to second section.

The first section may be for example substantially horizontal when using the system, in order to improve user comfort.

The second and/or third section may be substantially inclined and/or vertical.

The first, second and third section may fold into a "S" shape and/or spiral shape.

The foldable touchscreen may be attached to the system, associated with the system and/or detachable from the system.

At least the upper surface of the foldable touchscreen and optionally its sides may be made from the same material.

At least the upper surface of the foldable touchscreen and optionally its sides or the surface of the control module as a whole may be made from foldable glass.

The control module may have a smooth surface and/or be without any features, in particular without any relief and/or opening.

The sides of the module may comprise an elastomer and/or a watertight seal configured to form a hinge between the first and the second section and/or the second and the third section.

The system may be configured to display a first ultrasound image prepared by the ultrasound imaging system on the third section and/or a screen external to the system.

The system may further comprise duplication means configured to duplicate the first ultrasound image.

The duplication means may be configured to display the first ultrasound image, duplicated on the first and/or the second section, optionally in response to a predefined event or chain of events.

The duplication means may also be configured to drag and/or drop the first ultrasound image from the third section and/or from the external screen to the first and/or the second section, optionally in response to a predefined event, enabling the display of the first duplicated ultrasound image.

Thus, a duplication with a visual and intuitive effect is possible using the fact that the sections are connected.

The system may comprise processing means configured for determining a region of interest in the first ultrasound image by using a first predefined algorithm, the region of interest optionally constituting or forming part of the first duplicated ultrasound image.

The first duplicated ultrasound image can be displayed such that a user can mark a region on the latter and/or has annotation options via touchscreen inputs, for example a touch gesture.

Thus, the duplicated image can be used for taking notes directly on said image, for example by means of a stylus or touch interface (with one or more fingers).

In response, the processing means may be configured to process the first ultrasound image in accordance with the touchscreen inputs by using a feature of the predefined algorithm or a second predefined algorithm.

The processing means can be configured to display the first processed ultrasound image on the first and/or the second section.

The processing means can be configured to display the first processed ultrasound image on the third section and/or on a screen external to the system.

The predefined event may comprise at least one of the following elements:
- a voice, gesture or touch command of the user,
- a signal from a sensor of the system,
- a command triggered by an algorithm comprising, inter alia:
  - a predefined and/or customizable examination procedure algorithm, and
  - an artificial intelligence algorithm.

The first and/or the second predefined algorithm may comprise at least one of the following elements:
- a predefined and/or customizable image processing algorithm, and/or
- an artificial intelligence algorithm.

The present disclosure also relates to a medical imaging method using a system comprising:
- a foldable touchscreen with at least a first touchscreen section and a second touchscreen section, and/or an external screen and/or a third touchscreen section extending from said second section, the method comprising the steps:
- displaying a first ultrasound image generated by the ultrasound imaging system on the third section and/or the external screen of the system,
- duplicating the first ultrasound image,
- displaying the first duplicated ultrasound image on the first and/or the second section such that a user can mark a region on the latter and/or has annotation options via touchscreen inputs, or by using a stylus or voice commands, and
- in response, processing the first ultrasound image as a function of the touchscreen inputs by using a predefined algorithm.

For example, the images and/or annotations may be included in the report relating to the current examination.

The features and advantages of the disclosure will become apparent from the following description, given solely by way of a non-limiting example, and with reference to the accompanying figures. In particular, the examples illustrated in the figures can be combined unless there are obvious inconsistencies.

DESCRIPTION OF EMBODIMENTS

In the different figures, provided by way of illustration, the same reference numbers denote the same or similar elements.

An imaging system, for example for ultrasound, is typically an imaging device which is intended to provide images of a medium to be examined. In the case of medical an applications, this medium is generally a human or animal body, for example part of the body of a patient (muscles, embryo or fetus, breast, liver, abdomen, . . . ).

Recent user interface technologies, as used for example in smartphones or laptops, tablets, may also comprise foldable touchscreens. An example is described in document U.S. Pat. No. 10,318,042 B2.

A critical aspect during a medical examination and in the medical field in general is hygiene, more particularly the disinfection of the materials, tools and equipment used, in order to avoid contamination of the persons being examined and/or the user of the system. For this reason, the team in charge of an examination (comprising for example one or more ultrasound specialists, sonographers, doctors, technicians, assistants, . . . ) and/or the team in charge of cleaning and/or maintenance often have to disinfect the examination system, in particular after each examination or intervention, in particular, after each patient leaves or before a new patient arrives.

A user of the system may therefore include for example a member of a team in charge of an examination (comprising for example one or more ultrasound specialists, sonographers, doctors, technicians, assistants, . . . ) or a team in charge of cleaning and/or the maintaining the system.

Typical disinfection means comprise liquids, for example contained in a bottle or in the form of a spray or vapor. Alcohol is used for example as a disinfectant liquid. Other examples comprise hydrogen peroxide, quaternary ammonium, sodium hypochlorite, or a combination of some of these elements.

In this context, it may be problematic that an examination used is not resistant to disinfectants in all of its various parts, particularly, when they are used in liquid or viscous form. The parts concerned may comprise in particular each part of the system which may be in direct or indirect contact with the patient or the operator (for example a probe, a control module, handles, buttons, user interfaces, etc.). More particularly, the disinfecting liquids, such as for example alcohol (and/or hydrogen peroxide, quaternary ammonium, sodium hypochlorite, or a combination of these elements), may damage, abrade or deteriorate some materials and should therefore not be used in some cases or on certain areas of the system. On the other hand, even if some areas can be disinfected with a liquid, it may be difficult to do this reliably due to the specific shape of these areas (comprising for example interstices, features, different thicknesses, different materials, . . . ).

For example, any input means of a system user interface, comprising for example buttons, switches and/or rotary controls, may be regularly manipulated by the user and may therefore require disinfection after an examination. However, these areas may either not be resistant to liquids (in particular alcohol) or may be difficult to clean due to cavities between a button and an adjacent surface of a system housing for example. As a result, the person in charge of the examination and/or in charge of maintenance and/or servicing needs to be very scrupulous and careful and therefore has to spend a lot of time disinfecting the potentially affected areas. At the same time, the person needs to take care not to damage the system, for example by depositing too much liquid on the user interface, which could penetrate the system housing and damage said system.

In addition, in the event that the system is an ultrasound imaging system for example, the user generally has to apply a gel to the surface being examined and/or the surface of the probe being used. The gel can consist of a more or less viscous liquid, possibly composed of or having various different viscosities. This gel can also be potentially fouling or corrosive to the system or some parts of the system or at least complicate or disrupt the disinfection process, as the person responsible for the examination and/or for maintaining the system needs to ensure that the gel and the disinfectant liquid are applied correctly then removed and do not penetrate into the system housing. The gel can also increase the risk of inter-patient contamination and also has to be removed correctly for this reason. The fact that gel accumulates along with fouling can provide a suitable substrate for the growth of bacteria or other pathogenic elements. In particular, according to multiples clinical trials, it has been shown that ultrasound gel harbors and spreads infections. The gel can contribute to the increase of nosocomial infections, i.e. the spread of hospital-acquired infections, cf. for example: Esteban C. Nannini, Adriana Ponessa, Rosa Muratori, Patricia Marchiaro, Viviana Ballerini, Luis Flynn, Adriana S. Limansky "Polyclonal outbreak of bacteremia caused by *Burkholderia cepacia* complex and the presumptive role of ultrasound gel" The Brazilian Journal of Infectious Diseases 2015; 19(5); 543-545.

Furthermore, it is desirable to optimize the duration of each examination procedure in order to improve the comfort of the patient and reduce the associated cost. The preparation and cleaning steps of the systems also have to be safe and optimized to ensure the better use of said systems.

The present disclosure relates to medical imaging systems and methods using such a system. Such a system can consist of a medical examination system. More particularly, it can consist of an ultrasound wave imaging system.

Figure 1A:
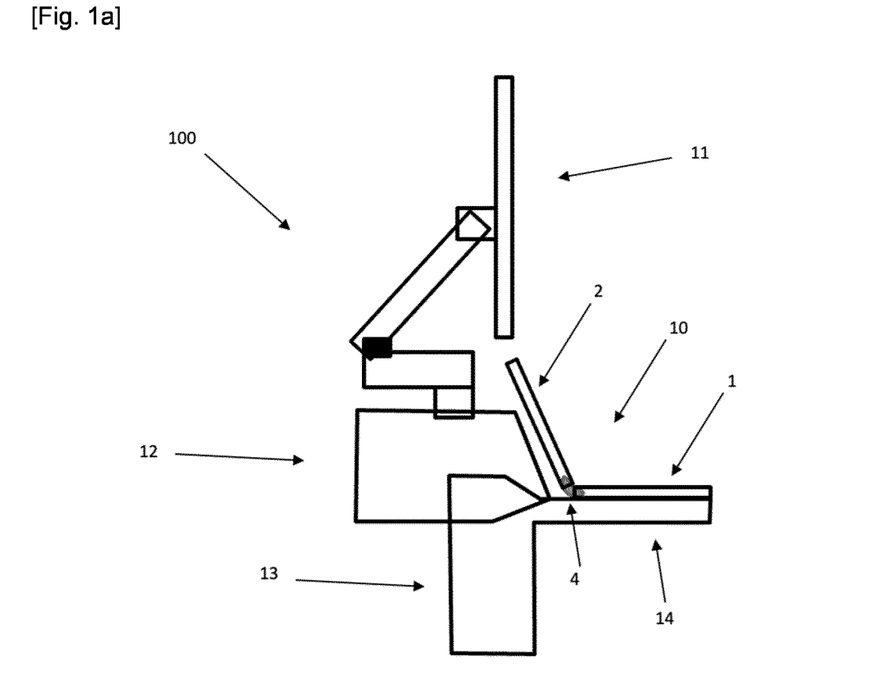
FIG. 1a illustrates schematically a first embodiment given by way of example of a system with a foldable touchscreen device according to the present disclosure, in a side view.

FIG. 1a shows schematically a first embodiment of a system with a foldable touchscreen device according to the present disclosure in a side view.

The system 100 can be medical imaging system (for example for examining a patient and/or veterinary use or any other imaging application), in particular an ultrasound system. However, the system can also be used in another other field where cleaning with liquids and/or disinfection are necessary or desirable. The system can comprise a control module 10 in the form of a foldable touchscreen device. In the following description, the terms "control module" and "foldable touchscreen device" can be used interchangeably. It is desirable that the whole system can be controlled by the foldable touchscreen device, for example in relation to each of the functionalities that can be used during its operation. In this manner, it becomes possible for a user (i.e. the person conducting the examination) to simply only touch the foldable touchscreen device and no other part of the system 10. As a result, it may be sufficient to only disinfect the foldable touchscreen device after the examination.

The system 100 can also comprise a main station 12 comprising for example electronic and/or computer means. The examples include a processing unit and/or one or more memory areas. Said computer means can be used for processing the examination data. However, it is also possible that the foldable touchscreen device 10 comprises such computer means or that these means are remote (for example at a workstation, in the cloud, . . . ).

The main station 12 can be connected to or may comprise one or more sensors and/or probes (not shown in FIG. 1a). One example comprises an ultrasound probe. Said sensors and/or probes can be configured to acquire examination information from a person undergoing examination and/or perform interventions.

The foldable touchscreen device can communicate with the main station 12 via a cable, but also alternatively via a wireless interface, for example using protocols such as WIFI®, BLUETOOTH® or the like. The main station can also supply electric power to the foldable touchscreen device, which can also be performed wirelessly or via a connector.

The main station can be placed on a stand or a base 13 (not shown fully in FIG. 1a). In particular, the stand or the base 13 can have a height adapted to or adaptable to the height of a user, i.e. such that the foldable touchscreen device is at a suitable height for the user and/or adaptable to the type of examination undertaken.

The system 100, in particular the main station 12, can also comprise and/or be associated with an external screen 11. Said external screen 11 can be arranged above the foldable touchscreen device. However, the external screen 11 can also be remote from the system, and be located for example in another room, another building or another site remote from the system. As a result, the external screen can also be provided for a second user. In other words, a first user can operate the system and a second user can examine the acquired data on the external screen.

The foldable touchscreen device comprises a first section 1 and a second section 2. The first section 1 can be arranged to be substantially horizontal. For example, it can be placed on a corresponding base plate 14 of the main station 12 or of the system 100, in particular, in a removable manner. The base plate can comprise communication and/or electric power means, in particular, for wireless communication and/or wireless power supply. In addition, it can comprise mechanical attachment means for fixing the foldable touchscreen device and/or optionally mechanically detaching it therefrom as required and preferred.

It is desirable that the base plate 14 is also resistant to disinfecting liquid. Consequently, in the event that the user accidentally applies liquid to the plate 14 or that the liquid spills on it from the foldable touchscreen device, the system cannot be damaged. For this reason, the base plate 14 can have a protective surface respectively and/or no opening to the electronic components inside the system.

The second section 2 extends from the first section 1 in a foldable manner. In an operational position, it can be tilted for example. Optionally, the angle of inclination can be selected freely by the user or predetermined.

As described in more detail below, the foldable touchscreen device can comprise a surface resistant to disinfecting liquids, such as for example alcohol. Said surface is in particular arranged on the touch side of the foldable touch device, but optionally also between the first and the second section (i.e. where the touch surfaces of the first and second sections meet) and on their sides. Consequently, when the person conducting the examination or another user cleans the touch surfaces with a disinfecting liquid, the foldable touchscreen device cannot be damaged, even though the liquid may reach the sides of the foldable touchscreen device or an area located between the first and the second section.

In addition, because the touch surfaces and optionally the side surfaces of the foldable touchscreen are substantially flat, the foldable touchscreen can be cleaned easily, rapidly and in a reliable manner. This can also apply to the area between the first and the second section. As a result, the system can accelerate the complete and reliable disinfection process more rapidly, more reliably and/or more thoroughly.

In an alternative, the entire surface of the foldable touchscreen device is resistant to disinfecting liquids, such as alcohol for example. In other words, the rear face of the first and the second section (which cannot be a touch surface) can also include this surface.

In addition, in an area on the sides of the foldable touchscreen device, where the first and second are connected, an elastomer or seal 4 may be provided. This elastomer or seal can in particular cover and/or protect a hinge or a seal between the first and the second section. This hinge or articulation can be configured to allow folding of the second section relative to the first section. The same features can apply to the intersection between the second and third section (cf. FIG. 2a). The folding angles can be predefined, constrained or their use can be selected freely by the user.

In addition, the system may be configured to be usable with (or can comprise) mechanical buttons (for example one or more clickable wheels) that can be placed on the foldable screen. It can communicate with the wireless system, for example via Bluetooth®. These buttons can be removed/detached/disassociated from the screen when being disinfected. The buttons can also shave a leaktight surface resistant to liquids and therefore be configured to be cleanable by a disinfectant liquid.

Figure 1B:
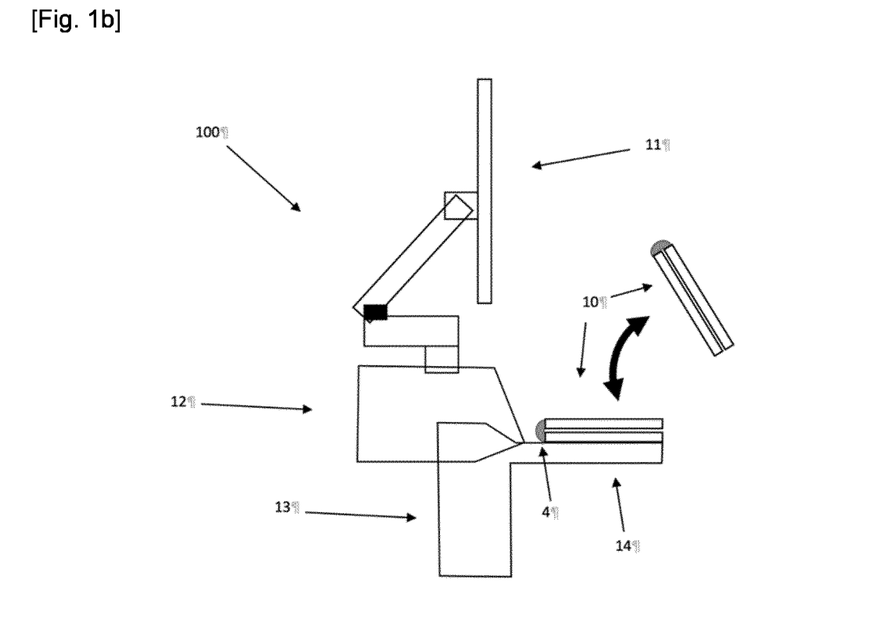
FIG. 1b shows schematically a first embodiment of the system of FIG. 1a, in which the foldable touchscreen device has been removed.

FIG. 1b shows schematically a first embodiment of the system of FIG. 1a, in which the foldable touchscreen device has been removed. As illustrated, the foldable touchscreen device can be closed on itself so that the touch surfaces of the first and second sections are adjacent to one another and within the closed foldable touchscreen device, advantageously providing 'mechanical' protection to the device. Alternatively or in addition, the foldable touchscreen can also be reclosable, such that the touch surfaces of the first and second sections are on the external side of the closed foldable touchscreen device.

As a result, the foldable touchscreen device, when mechanically disconnected from the main station can also be used remotely from the main station 12, for example for driving and/or controlling the system 100 more freely, and/or for other safety, ergonomic functions. In addition, once removed, the base plate 14 can be disinfected on its upper surface, if necessary.

Figure 1C:
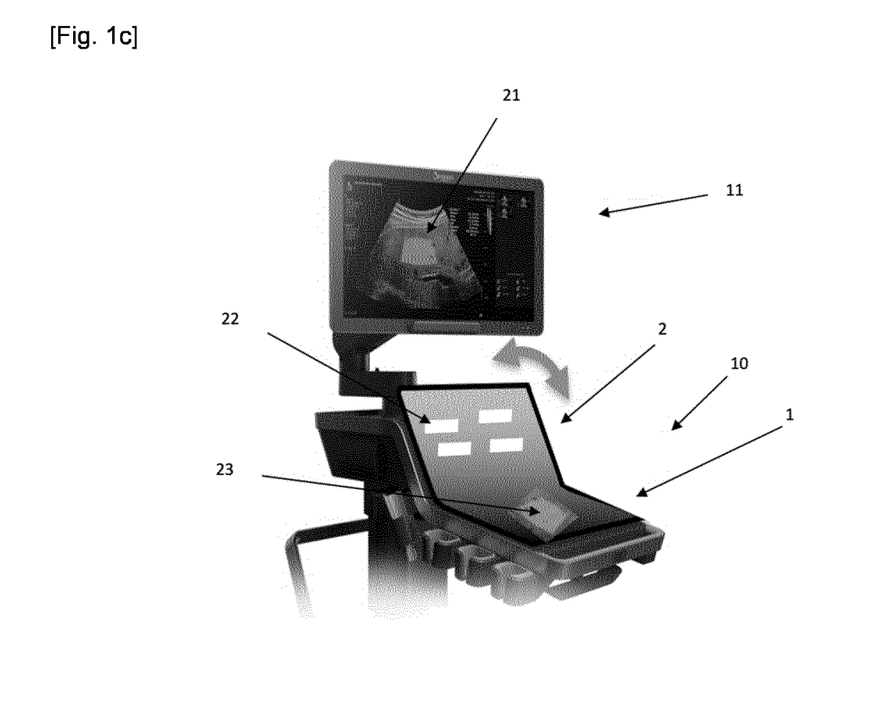
FIG. 1c shows schematically the first embodiment of the system of FIGS. 1a and 1b in a perspective view.

FIG. 1c represents schematically the first embodiment of the system of FIGS. 1a and 1b in a perspective view.

Figure 2A:
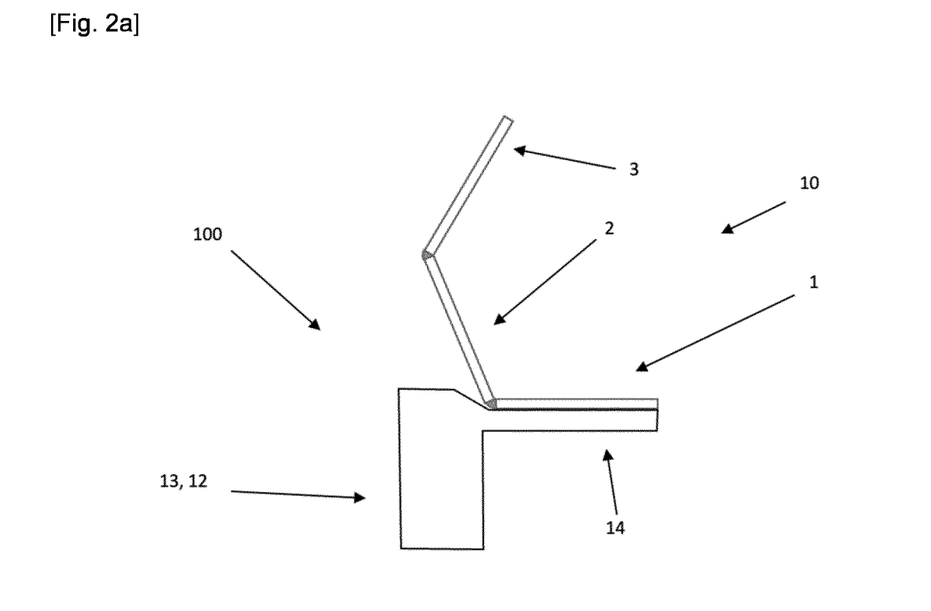
FIG. 2a shows schematically a second embodiment of a system with a foldable touchscreen device according to the present disclosure in a side view.
Figure 2B:
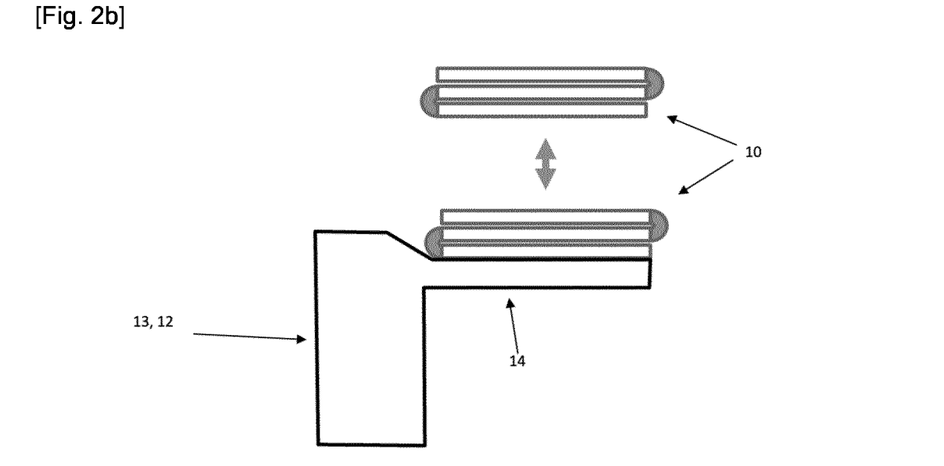
FIG. 2b shows schematically the second embodiment of the system of FIG. 2a, in which the foldable touchscreen device has been removed.
Figure 2C:
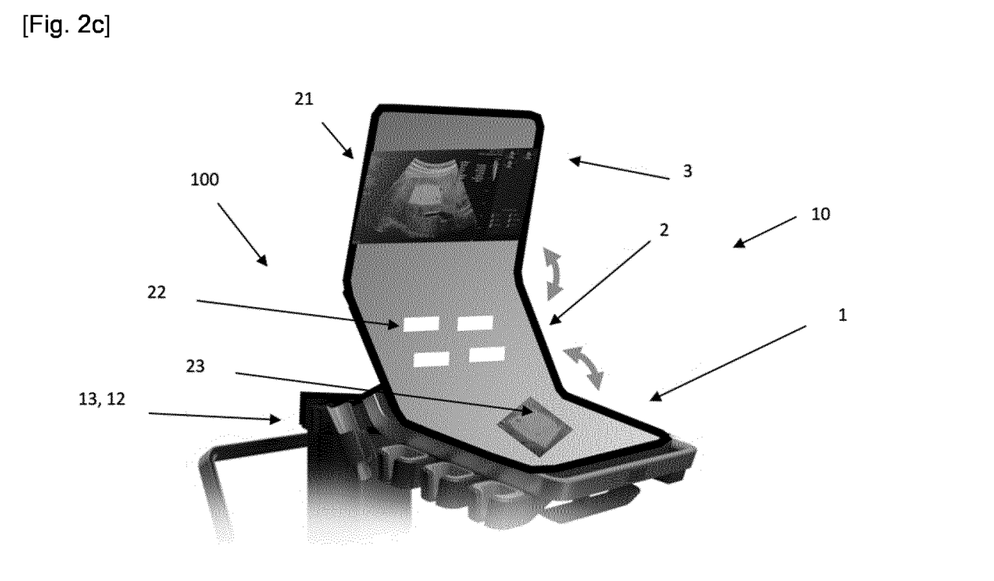
FIG. 2c shows in a schematic manner the second embodiment of the system of FIGS. 2a and 2b in a perspective view.

The example shown also illustrates possible display functions which will also be detailed in the context of FIG. 2c. It should be noted that these functions and features may also apply to two embodiments. As a result, the optional external screen 11 of FIG. 1c can be replaced or may also be provided to the optional third section 3 of the foldable touchscreen device 10.

The external screen 11 can display examination image data and/or an examination image 21 acquired by the system. The second section 2 of the foldable touchscreen device (which can be arranged between the first section and the external screen) may make it possible to display additional setting options, i.e. control means 22 (for example in the form of buttons, switches and/or rotary controls and/or cursors) which can be configured to control the examination procedure. The examination procedure can comprise for example the acquisition of examination data and/or processing data.

The first section 1 can display a duplicated portion 23 of the image and/or image data 21 of the external screen 11. Said portion can be for example a region of interest of the image 21. Said region of interest can be selected manually by a user and/or automatically by a procedure implemented by the system. For example, it can be a region of interest with specific image data included in a larger image. For example, the image 21 can comprise B mode image data (brightness mode) and the region therein can comprise (instead of or in addition) ShearWave™ or SWE (shear wave elastography) image data. In addition or alternatively, the region of interest can be selected automatically by an algorithm of the system. Examples of such algorithms comprise an AI(artificial intelligence)-based algorithm and/or algorithms involved in the management of predefined and/or parameterizable or adjustable examination procedures(s).

The organization of the display information according to one example has the advantage that a user can easily control the examination using control means 22. These control means 22 are easily accessible by the user and clearly visible, when the user is concentrating for example on the external screen 11 and/or is acquiring data using a probe and/or a sensor for example. In addition, the portion of the image 23 displayed on the first section allows the user to approach it and look at it very closely if necessary. The user can for example make annotations using an electronic pen or one or more fingers. These annotations can be used by the system to prepare, parameterize and/or execute other data processing steps, as explained for example in the context of the FIG. 2c. In other words, because the first section is optionally arranged substantially horizontally, it can be used as a drawing table by the user, making it easier to make annotations and/or mark areas, etc.

However, it should be noted that the information displayed can also be organized in another way on the different screens. For example, the system may be configured to allow a user to freely select which information is displayed in which area, for any examination being carried out (user profile), for the whole period of examination, or for certain steps of the examination. At least on the foldable touchscreen device, this can be performed by a "drag and drop" gesture. In addition, at least information displayed on the first section can be interchangeable with information displayed on the second section. In other words, the functions of the first and the second section can be interchangeable.

The illustrated example of the foldable touchscreen device 10 includes a border. However, the screen can also be borderless, as explained for example in the context of FIGS. 3a and 3b.

FIG. 2a represents schematically a second embodiment of a system 100 with a foldable touchscreen device according to the present disclosure, in side view.

The second embodiment corresponds to the first embodiment of FIGS. 1a to 1c, the main differences being described in the following. In the second embodiment, the foldable touchscreen device can comprise three foldable sections 1, 2, 3. As a result, the third section 3 can extend from the second section 2 and can be foldable and/or curved relative to the second section.

Said third section 3 can replace the external screen 11 shown in the first embodiment or can be provided in addition to said screen. In the event that the system 100 does not include an external screen 11, the shape of the main station 12 can also be adapted. For example, the electronic and/or computer means can be integrated into the stand and/or the base 13. The main station also be shaped substantially in the form of a desk, with the base 14 on its upper side.

FIG. 2b represents schematically the second embodiment of the system of FIG. 2a, wherein the foldable touchscreen device has been removed/disconnected.

The foldable touchscreen device can be removed from the main station 12, i.e. the base plate 14. As illustrated, the three sections of the foldable touchscreen device can be folded (i.e. bent) into a zigzag or S-shape. Alternatively or additionally, they can be folded into a spiral shape.

FIG. 2c shows schematically the second embodiment of the system of FIGS. 2a and 2b in perspective view. The information displayed may have an organization corresponding to that shown in FIG. 1c. As a result, the functions and the features of the displayed information can correspond to those of FIG. 2c. In the example of FIG. 2c, the third section replaces or completes the external display (screen, projector, . . . ).

Since the three sections are connected without any border between them, different visual effects and/or control functions become possible, which facilitate the use of the system and optimize the work of the user.

For example, the system may be configured such that a user can move any displayed information (or item of displayed information) from any position to another. This is not only possible within a section but also from one section to the other. Such a movement can be controlled by a touch gesture by the user, for example "drag and drop".

In another example, the portion of the image 23 can be dragged or switched from the third section to the first section (for example via the second section). Due to the borderless joints between the sections, such a visual effect can be achieved without interrupting the display of the portion of the image 23. Optionally, the image can be displayed transparently during the dragging, such that any other displayed information (for example the control means 22) is not completely hidden and always remains at least partially visible. Such a visual effect can have the advantage that a user can easily understand where the duplicated image 23, i.e. the (original) image 21, comes from. As a result, a more intuitive examination procedure becomes possible.

Such a visual effect can be triggered for example automatically by a process executed by the system, as explained in the context of FIG. 1c. However, it can also be triggered manually by a user. For example, the user can mark a specific area in the image 21 or select a predetermined region of interest (for example a SWE image inside a B-mode image). Due to the borderless connections of sections 1 to 3, it becomes possible for the user to move the selected portion of the image (or otherwise also the complete image 21) with a touch gesture/function (for example "drag and drop") to another section, for example section 1. In addition, the system may be configured such that the portion of duplicated image 23 can be enlarged relative to the original image portion in the image 21. Such a zoom function can be performed automatically by the system and/or the system can provide means for manual zooming.

The user can make annotations in the duplicated image 23 and/or mark a region in the duplicated image. For example, the user can use an electronic pen of the system and/or a finger to do this. Optionally, the user can make other control gestures, for example using one of the control means 22. In one example, the user can set a parameter using a sliding controller 22 or a virtual button. In another example, the user can select a command, for example by touching a button 22. In response, the system (in particular, its computer means) may be configured to process the image 23 and/or 21. For example, the image 21 can be processed to better highlight specific features or areas in response to the user's gesture in the image 23. This process makes it easier for the user to work more easily with the image data acquired by the system (for example using increased duplication of the region of interest displayed in the first section). Thus, more reliable and more rapid data analysis becomes possible (for example using the processed image 21 displayed in the third section).

The visual effects and/or control functions described above can also be implemented in the first embodiment, at least with regard to the first and the second section. In addition, an external screen can also be configured for these visual effects and/or control functions. The external screen can for example also be a touchscreen, making it possible inter alia to perform the said touch gestures. The external screen and the foldable touchscreen device of the first embodiment can also be arranged so that there is little or no space between the external screen and the second section (cf. for example FIG. 1a). The external screen can also comprise a borderless display.

Figure 3A:
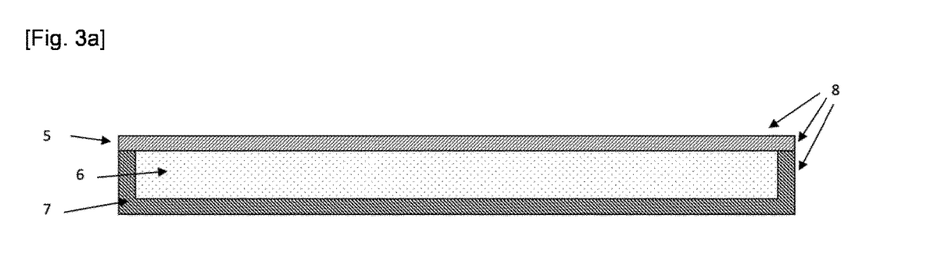
FIG. 3a shows schematically a first embodiment according to an example of the surface structure of the foldable touchscreen device according to the present disclosure.

FIG. 3a shows schematically a first embodiment according to an example of the surface structure of the foldable touch device according to the present disclosure. More particularly, FIG. 3a shows schematically the foldable touch device in a side view. The illustration of the foldable touch device is very schematic, it does not illustrate the foldable joints between two sections. The illustration can correspond for example to a single section, for example show a lower side of the first section.

The foldable touchscreen device can comprise a touchscreen 5 with a protective surface 8. Below the screen 5, an electronics compartment 6 can be arranged inside the foldable touchscreen device. The electronics compartment 6 can comprise electronic components and/or computer means. For example, a processing unit and/or a memory and/or a rechargeable battery.

The foldable touchscreen device can comprise a protective cover on its sides and bottom, i.e. for example on all sides except the one on which the touchscreen 5 is arranged.

The touchscreen 5 can be arranged without borders over the whole upper surface of the foldable touchscreen device. As a result, the whole upper surface can be used like a screen. This upper face can also be considered as the touch surface. The protective surface 8 can also be arranged on the sides of the foldable touch device and possibly also on the surface of the protective cover 7.

The protective surface 8 is optionally made from a material that is resistant to liquids, more particularly to disinfecting liquids, for example alcohol. An example of such a material is glass. Another example comprises a plastic material (for example Plexiglas, transparent PVC film) or sapphire glass which is configured not to be damaged by the disinfecting liquids, for example alcohol. At least in the foldable areas between two sections, the surface material has desirable characteristics to allow a corresponding bending or flexing movement. For example, a glass material used can be thin enough to allow such bending, at least in these areas.

In this manner, the foldable touchscreen can advantageously be cleaned with a liquid and/or disinfected by applying a disinfecting liquid to any of its surfaces, in particular its touch surface.

In other words, given that the screen 5 and/or at least the surface 8 covers the entire upper surface, there are no openings or spaces where the liquid could penetrate and damage the electronic components.

Figure 3B:
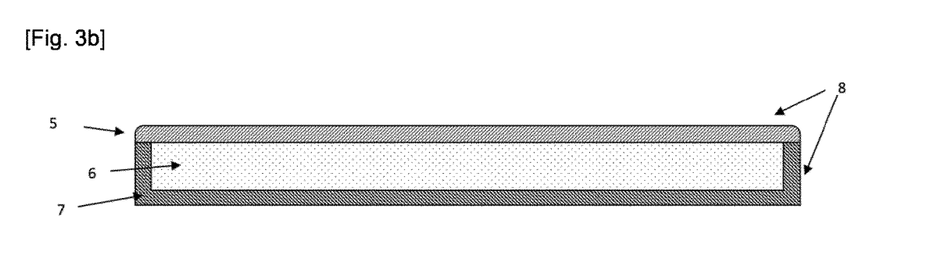
FIG. 3b shows in a schematic manner a second example of the surface structure of the foldable touchscreen device according to the present disclosure.

FIG. 3b shows schematically a second embodiment, according to one example, of the surface structure of the foldable touch device according to the present disclosure.

In general terms, the second embodiment according to one example may correspond to the first embodiment of FIG. 3a. However, the touchscreen 5 may be arranged not only over the whole upper surface of the foldable touch device, but also, at least partially, over its side faces. In other words, the touchscreen 5 can be folded on its sides around the electronic compartment 6. The protective surface can be arranged on at least one outer surface of the touchscreen 5. Also in this embodiment the protection of the touchscreen 5 can thus be achieved.

Figure 4A:
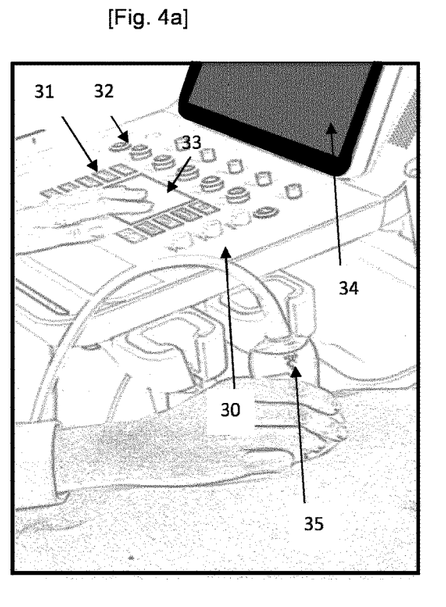
FIG. 4a shows schematically a conventional control module including mechanical keys and a touch pad.

FIG. 4a shows schematically a conventional control module 30 including mechanical keys 31 and a touch pad 33. The control module can comprise other known input means, such as rotary buttons 32. As illustrated, the user generally uses one hand to hold the probe 35 in contact with the patient and the other to control the system, i.e. its control module. Typically, the user has to concentrate on the probe and on the screen 34 at the same time. Consequently, the user tries to control the control mode blindly (i.e. without looking at it) as far as possible. In addition, the user is generally in a dark room, which is more conducive to analyzing images displayed on the screen. In this context, the user can thus benefit from the fact that the keys are physical keys which intuitively provide tactile feedback to the user and guide them in manipulating the buttons using their sense of touch. However, when using a conventional touchscreen as a control module, the user may not have this advantage of haptic feedback and may therefore be required to additionally concentrate visually on the control module. For this reason, the present disclosure provides a solution in which the user can systematically, according to their requirements, use the touchscreen without looking at it, i.e. in a blind manner.

Figure 4B:
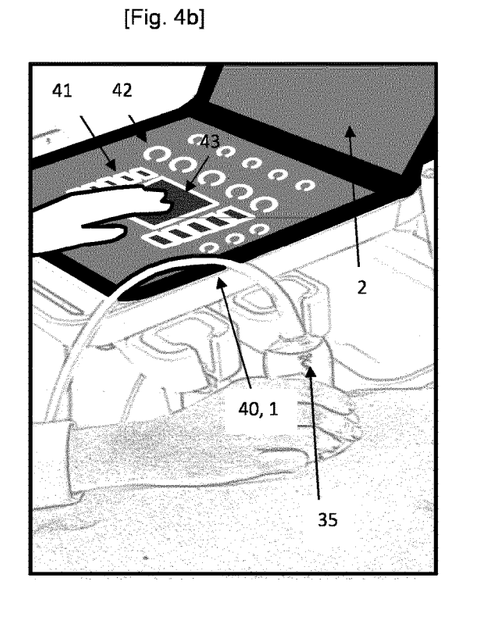
FIG. 4b shows schematically the foldable touchscreen with a user interface in a predefined mode according to the present disclosure.

FIG. 4b shows schematically the foldable touchscreen with a user interface in a predefined mode according to the present disclosure. The foldable touchscreen can correspond to the touchscreens described above, and can in particular comprise a plurality of sections 1, 2 and 3. At least one of the sections can have a user interface 40 including a plurality of control means. In the present example, the first section 1 can comprise the user interface. However, the user interface can also be represented on any other section or a combination of sections. It is also noted that for the technology shown which enables blind control of the system, it is not necessary for the touchscreen to be foldable or comprise multiple sections.

The user interface 40 can comprise a predefined mode, wherein the user interface is configured to position the control means in a predefined manner. Thus, in this mode, the position of the control means can be predefined, for example in the form of keyboard, a set of keys, buttons. This mode can be used as a standard mode, for example when the system is started up and no functioning mode or examination procedure has been commenced yet. It should be noted that the control means in the predefined mode do not necessarily have to be same as in the adaptive mode. For example, in the adaptive mode, only a selection of control means can be used, as described below.

For example, the user interface in its predefined mode can correspond mainly to a conventional control module, as illustrated in FIG. 4a. Users can choose, can be offered by default or on request, a configuration close to the button/keypad configurations usually used in the machines which they are used to using, so as to reproduce their known work environment, while offering the many advantages set out in connection with the present disclosure. Thus, the touchscreen can have control means which may correspond to conventional means, for example one or more buttons 41, a touch pad and/or a track ball 43, a wheel (not shown), and one or more rotary buttons 42.

As the control means are not physical buttons, the touchscreen may be configured and/or adapted to the user by learning or parameterization to simulate haptic effects, i.e. a tactile stimulus perceptible to a user's hand and/or fingers. In particular, a mechanical button (for example a click command) and/or the shape of a control means can be simulated in this manner. For example, the haptic effects can make is possible increase or reduce the surface friction. For this purpose, the high-frequency sound waves or electrical pulses can be used. In another example, micro-fluidic inputs can be used.

The control means can therefore be understood to be virtual or simulated means, as they are provided by the touchscreen, but are not separate physical devices. This also has the advantage that the interface is very easy to clean.

The control means can be defined by simulating a haptic and/or structural shape of the control means on the touchscreen, for example a border, a button rim. For example, in the event that the control means is a touch button, the simulated border can help the user to feel where the button is. This makes blind operation of the control module easier and more reliable.

Figure 5A:
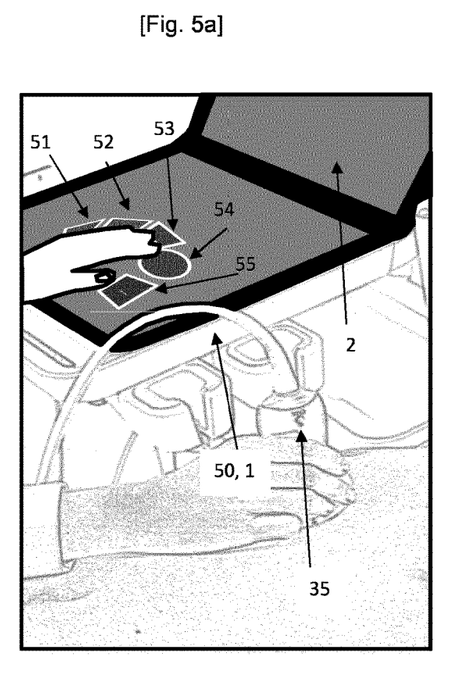
FIG. 5a shows schematically the foldable touchscreen with a user interface in an adaptive mode and a hand of a user in a first position according to the present disclosure.

FIG. 5a shows schematically the foldable touchscreen with a user interface in an adaptive mode and a hand of a user in a first position according to the present disclosure. The example of FIG. 5a can correspond substantially to that of FIG. 4b. However, instead of the predefined mode, here the user interface 50 has the adaptive mode.

In the adaptive mode, the user interface can be configured to position the control means 51-55 according to a gesture of the user. For example, the gesture of the user can consist of placing a hand (for example the palm and/or one or more fingers or the whole hand) on the touchscreen or at least approaching the touchscreen with the hand.

Alternatively or additionally, the gesture of the user may consist of placing (and/or at least approaching) an external control device on the touchscreen. For example, the control device can be mechanical button, a control wheel or a joystick. The touchscreen can also display the functions of the various different control means.

Figure 5B:
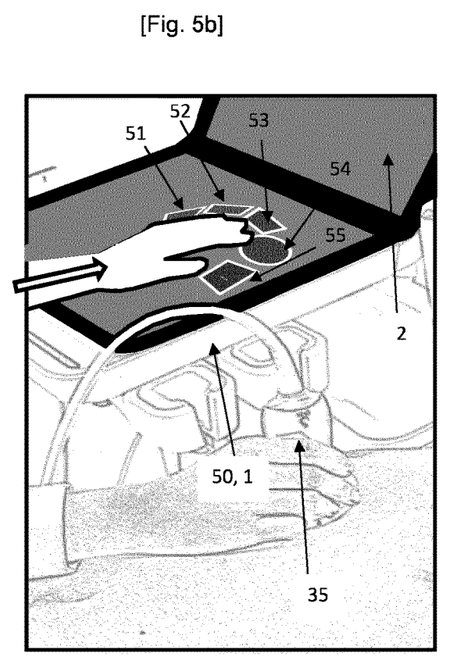
FIG. 5b shows schematically the foldable touchscreen with a user interface in an adaptive mode and a hand of a user in a second position according to the present disclosure.

Consequently, the positioning of the control means can depend on the place in which the user has put their hand or the external control device on touchscreen. The control means can therefore always be positioned so as to correspond with the position of the hand, as can be seen in the comparison of FIGS. 5a and 5b. The user can therefore place their hand anywhere on the touchscreen and control the system without looking at the touchscreen, i.e. blindly.

For example, the user interface can switch from predefined mode to adaptive mode on the basis of a recognized gesture of the user, for example when the user places their whole hand or at least their palm on the touchscreen. In this way, the system and/or the control model can recognize that the user is not paying attention to the predefined mode (i.e. predefined control means) and that this adaptive mode is preferred by the user and/or is more appropriate in this phase of use.

Optionally, a command is only triggered by a control means if the user has clicked or actuated the control means intentionally. This means that it can be desirable that simply touching the touchscreen does not trigger the command. Consequently, any control means that is unintentionally tapped or touched will not trigger a control. This further improves the blind use of the control module. For example, the touchscreen can comprise a touch panel with one or more pressure sensors. Using these sensors, the touchscreen may be configured to distinguish between a simple touch and an intentional selection, for example a click.

As illustrated in FIG. 5a, in the adaptive mode, the user interface can be configured to position a control means in a position where it is determined that a finger (or in particular the pad or the tip of the finger) touches (or approaches) the touchscreen. As a result, the position can be determined as a function of the position where the hand is placed on the touchscreen, in particular, the palm and/or the finger. For example, depending on the area touched by the palm, the size of the hand and therefore the position of the finger can be estimated by the control system or module. Furthermore, a type of finger (for example the index finger or thumb) touching the touchscreen can be identified according to the position of the palm and/or other fingers touching the touchscreen. In this context, it is also possible to detect if this is a finger of the left hand or the right hand. This makes it possible to assign a specific control means or a specific command to a specific type of finger, for example "freeze image" to the thumb.

The system and/or the control module can thus be configured to determine the position of a finger (or in particular the pad of the finger) according to the user's gesture and to position a control means at the determined position. The size of the hand and/or of the finger can thus also advantageously be taken into account by the system.

In addition, in the adaptive mode, a selection of control means can be position which is selected as a function of a system operating mode and/or a workflow, for example predefined and/or user-adapted examination procedure or an algorithm. This algorithm can comprise inter alia: a predefined and/or customizable medical workflow algorithm, and an artificial intelligence algorithm. Thus, the system and/or the control module can select only certain control means (i.e. certain commands) which are frequently used in the current mode of operation. As these selected control means (for example up to five) can be positioned so as to correspond to the position of a single finger, the user can control the system blindly, simply by placing their hand anywhere on the touchscreen.

For example, a specific control means (i.e. a specific command) can be attributed to a specific finger. In this manner, the user can recover this control means without looking at the touchscreen. For example, at the location of the thumb, a "freeze" button 55 can be positioned which freezes the acquired image. In another example, in the position of the index finger, a "select" button 54 can be positioned, which selects a currently available option (for example, displayed at the same time on the touchscreen). In another example, at the position of the middle and the ring fingers, a control means in the form of a track ball 53 and/or a touch pad 52 can be positioned. In a further example, a control means 51 with a freely selectable function can be positioned at the location of the little finger.

In addition, a control means may be configured to be controlled by using two or even more fingers together. In addition, more than one control means can also be assigned to one finger. For example, successively during a protocol sequence or during a personalization exercise for a user or training in the use of the system.

In general, other kinds of control gestures than a simple control click are also possible. For example, a double click can be used, a click with several fingers together or a scrolling and/or scanning, zooming in/out gesture, with one or more fingers.

It should be noted that the positions and the types of control scan also be different and/or configured by the machine according to the use made of it and/or configured for the user according to their preferences. In particular, it is possible that users can select the positioning themselves. The adaptive mode can therefore be specific to the user, such that each user can have their own adaptive mode. In addition, the adaptive mode and/or the selection of the control means can not only be specific to the user but also to the current operating mode of the system, as described above.

It is also possible that the system and/or the control module are configured such that the functions associated with a control means assigned to a specific finger evolve automatically during an operation mode according to a predefined workflow. In this way, it becomes possible that the user can trigger a sequence of commands with a single finger, each command being applicable at a given movement during the operating mode. In this manner, the user's workflows can be semi-automated by the system. Examples of workflows are provided below.

It is also possible that the control means are attributed to the fingers, such that the user can trigger them in a specific sequence during a workflow. This can help the user remember the sequence easily, such as when playing a melody on a piano.

Examples of different modes of operation in an ultrasound system can be a B mode (brightness mode), a ShearWave™ mode (Shear Wave Elastography), a Doppler mode, combinations of these modes and/or other types of ultrasound acquisition modes.

An example of the workflow during ultrasound acquisition can be as follows:
- in a first operation, the user can select a specific ultrasound acquisition mode. Respective control means for selecting different types of ultrasound acquisition modes can be assigned to the fingers in this operation, for example mode B to the index finger. The user can select a mode by clicking with a finger, for example the index finger. As a result, the ultrasound acquisition is started in the selected mode.

In a second operation, the user configures one or more ultrasound acquisition parameters. Respective control means for configuration can be allocated to the fingers in this operation. In one example, the index finger can be assigned to a "gain" offset controller, and/or the thumb can be assigned to the "freeze" operation to stop the ultrasound acquisition.

In a third operation, the user can start a video or take a screenshot. The respective control means can be assigned to the fingers in this operation, for example taking a screenshot of the can be assigned to the index finger, and starting a video to the middle finger.

In the case of a video recording, in a fourth operation, the user can stop the video, again with respectively assigned control means, for example again with the middle finger.

Depending on what the user has selected, in a fifth operation, the user can view the video or display the screenshot. Other control means for saving the video or the screenshot, deleting the video or the screenshot and other functions can be assigned to other fingers in this operation.

As a result, the user can be proposed at each step of the workflow only applicable and/or relevant commands while non-applicable or irrelevant commands may disappear. It may be desirable however that some commands remain in several or even all available operations and assigned to the same finger, for example the "freeze" operation assigned to the thumb. This can help the user maintain an overview of the most important commands and advantageously help them to intuitively set up optimized sequences of the use of the system. This can advantageously prevent oversights and/or drastically reduce examination times.

FIG. 5b shows schematically the foldable touchscreen with a user interface in an adaptive mode and a hand of a user in a second position according to the present disclosure.

The example of the FIG. 5b corresponds substantially to the example of FIG. 5a.

However, the control means 51-55 are repositioned according to the position of the hand on the touchscreen. Thus, since in the example in FIG. 5b, the user has moved (or moved away from the touchscreen then moved towards or rested on the touchscreen) their hand to another position than in the example of FIG. 5a, the control means have been repositioned automatically as a result. The user can for example lift their hand and place it back on the touchscreen, at any position on the touchscreen, potentially very different from the previous one in terms of its location, its orientation, . . . (for example due to a necessary movement of the probe), without having to concentrate on the touchscreen. Thus, advantageously, the user can continue to control the touchscreen in the same way as before (i.e. as they did in the previous position of their hand). In other words, the touchscreen and in particular the positions of the controls adjust to the user.

If the user lifts their hand from the touchscreen in adaptive mode (optionally at least for a predefined minimum period), the touchscreen can also switch automatically from the adaptive mode to the predefined mode. The changes between the modes can also be triggered specifically by the user.

In another example, the user can drag or drop their hand on the touchscreen from a first position (for example the position in FIG. 5a) to a second position (for example the position in FIG. 5b) and the control means 51-55 can follow their fingers. Such a movement may be due for example to a required movement of the probe which is held in the user's other hand or to any other movement of the user. In this example, the system and/or the control module may be configured to determine that at least some parts of the hand, for example the palm and/or at least one finger (or alternatively two or all of the fingers) remain in contact with the touchscreen when moving from the first position to the second position. On the basis of this determination, the movement of the hand can be interpreted as a movement which therefore requires a respective readjustment of the control means 51-55, for example an unintentional movement. In the same manner, it may be possible for a user to reposition the position of the control means 51-55 by remaining in contact with the control means and moving the control means 51-55 to another position, for example a more comfortable position.

Figure 6A:
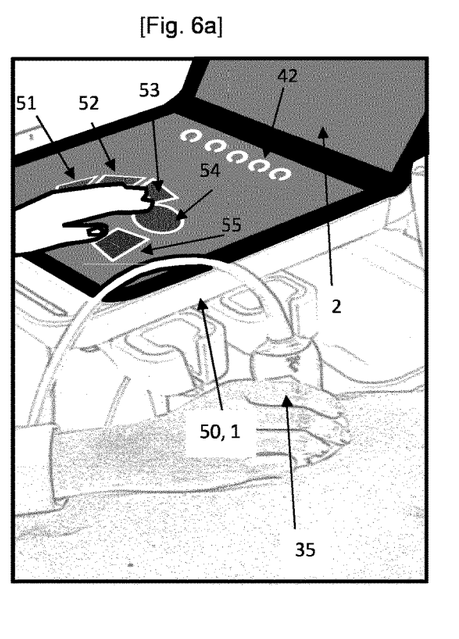
FIG. 6a shows schematically the foldable touchscreen with a user interface in a combined adaptive and predefined mode and a hand of a user in a first position according to the present disclosure.
Figure 6B:
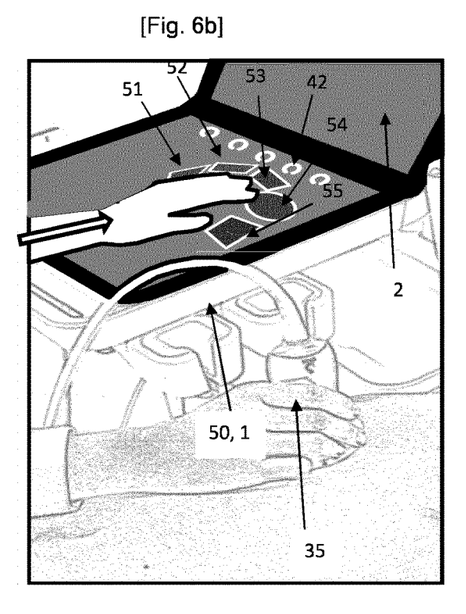
FIG. 6b shows schematically the foldable touchscreen with a user interface in a combined adaptive and predefined mode and a hand of a user in a second position according to the present disclosure.

FIG. 6a shows schematically the foldable touchscreen with a user interface in an adaptive and predefined mode and a hand of a user in a first position according to the present disclosure. FIG. 6b shows schematically the foldable touchscreen with a user interface in a combined adaptive and predefined mode and a hand of a user in a second position according to the present disclosure.

The examples of FIGS. 6a and 6b correspond substantially to the examples of FIGS. 5a and 5b, respectively. However, in the combined adaptive and predefined mode, the user interface comprises not only a first set of control means 51-57 which are positioned according to a gesture of the user (for example a position of the hand), but also a second set of control means 42 in predefined position. Thus, while the first set changes position according to the gesture of the user, the second set always remains in its predefined position. In this manner, frequently used functions can be assigned to the first set 51-55 and at least one peripheral region of the touchscreen can still be used for the second set. As a result, the user can operate the first set without having to look at the touchscreen and can also use other functions.

All of these embodiments and other examples as described above are given by way of a non-limiting example only and may be combined and/or modified within the scope of the following claims.

The invention claimed is:
1. A medical imaging system comprising:
 a control module configured to control the medical imaging system, the control module including a foldable touchscreen with at least a first touchscreen section and a second touchscreen section, the second touchscreen section extending from said first touchscreen section and being tiltable relative to said first touchscreen section via a hinge connecting the first touchscreen section to the second touchscreen section, wherein the control module has a watertight surface resistant to liquids configured to be cleanable by disinfectant liquid on the first touchscreen section and the second touchscreen section, and between the first touchscreen section and the second touchscreen section;

wherein the foldable touchscreen comprises a third touchscreen section extending from the second touchscreen section and being tiltable relative to the second touchscreen section; and wherein at least one of the sides of the module comprises an elastomer configured to form a sealed hinge at least one of between the first touchscreen section and the second touchscreen section, and between the second touchscreen section and the third touchscreen section.

2. The imaging system according to claim 1, wherein at least one of the first touchscreen section and the second touchscreen section is configured to function as an element for controlling and/or regulating the system.

3. The imaging system according to claim 1, wherein at least one of the first touchscreen section and the second touchscreen section of the foldable touchscreen is configured to display a user interface.

4. The imaging system according to claim 3, wherein the user interface comprises an adaptive mode, wherein the user interface at least one of is configured to position a controller according to a gesture of the user, and/or the user interface comprises a predefined mode, wherein the user interface is configured to position the controller in a predefined manner.

5. The imaging system according to claim 4, wherein the gesture of the user comprises placing at least one of all or part of the hand and an external control device on the foldable touchscreen.

6. The imaging system according to claim 4, wherein in the adaptive mode, the user interface is configured to position a controller in a position associated with a position of a finger on or close to the touchscreen.

7. The imaging system according to claim 4, wherein in the adaptive mode, a selection of controllers is positioned, the controllers being selected based on an operating mode of the system.

8. The imaging system according to claim 3, wherein the user interface comprises at least one of: additional regulating options, a controller, all or part of a patient file, and an examination report.

9. The imaging system according to claim 1, wherein the foldable touchscreen is configured to simulate haptic effects, and comprises at least one of a mechanical button, a track ball, a touch pad, and a shape of a controller.

10. The imaging system according to claim 9, wherein the controller is defined by simulating at least one of a haptic form and a structural form of the controller on the touchscreen.

11. The imaging system according to claim 1, wherein at least one of the first touchscreen section, the second touchscreen section and the third touchscreen section fold into an "S" shape and/or a spiral shape, and the foldable touchscreen is detachable from the system.

12. The imaging system according to claim 1, wherein the system comprises an ultrasound wave imaging system.

13. The imaging system according to claim 1, wherein at least one of the watertight surface is resistant to liquids on sides thereof, and at least one of the upper surface of the foldable touchscreen and the sides thereof comprises the same material.

14. The imaging system according to claim 1, wherein at least one of the upper surface of the foldable touchscreen the sides thereof, and the surface of the control module is made as a whole of foldable glass.

15. The imaging system according to claim 1, wherein the control module at least one of has a smooth surface and is without features.

16. A medical imaging system comprising:

a control module configured to control the medical imaging system, the control module including a foldable touchscreen with at least a first touchscreen section and a second touchscreen section, the second touchscreen section extending from said first touchscreen section and being tiltable relative to said first touchscreen section;

wherein the control module has a watertight surface resistant to liquids configured to be cleanable by disinfectant liquid on the first touchscreen section and the second touchscreen section, and between the first touchscreen section and the second touchscreen section;

wherein the foldable touchscreen comprises a third touchscreen section extending from the second touchscreen section and being tiltable relative to the second touchscreen section;

the system being configured for displaying a first image generated by the imaging system on the third touchscreen section and/or an external screen of the system, the system further comprising: a duplicator configured to duplicate the first image and to display the first duplicated image on the first touchscreen section and/or the second touchscreen section in response to a predefined event.

17. The imaging system according to claim 16, wherein the first duplicated image is obtained by dragging and/or dropping the first image from the third touchscreen section or the external screen to the first touchscreen section or the second touchscreen section.

18. The imaging system according to claim 16, further comprising: a processor configured to determine a region of interest in the first image using a first predefined algorithm, the region of interest forming part of the first duplicated image.

19. The imaging system according to claim 18, wherein the first duplicated image is displayed such that a user at least one of can mark an area on the latter and has annotation options, wherein in response, the processor is configured to process the first image by using a functionality of the predefined algorithm or a predefined second algorithm.

20. The imaging system according to claim 19, wherein the processor is configured to at least one of:

display the first processed image on at least one of the first touchscreen section and the second touchscreen section, and display the first processed image on at least one of the third touchscreen section and on an external screen of the system.

21. The imaging system according to claim 16, wherein the predefined event comprises at least one of: a user command, a signal from a sensor of the system, a command triggered by an algorithm comprising at least one of a predefined algorithm, a customizable algorithm for the examination procedure, and an artificial intelligence algorithm.

22. A method for medical imaging using a system comprising:

a foldable touchscreen having a watertight surface resistant to liquids and having at least one of a first screen section and a second screen section, and a third screen section extending from said second screen section and being tiltable relative to the second screen section, the medical imaging system further comprising a hinge connecting at least one of the first screen section to the second screen section, and the second screen section to the third screen section, wherein the hinge comprises an elastomer configured to form a sealed hinge at least one of between the first screen section and the second screen section, and between the second screen section and the third screen section;

the method comprising:

displaying a first image generated by the imaging system on the third screen section of the system, duplicating the first image, displaying the first duplicated image on at least one of the first screen section and the second screen section such that a user can at least one of mark an area on the latter and have annotation options, and in response, processing the first image using a predefined algorithm.

* * * * *